United States Patent [19]

McClure

[11] 4,041,090
[45] Aug. 9, 1977

[54] ETHYLBENZENE PROCESS USING AN UNSUPPORTED PERFLUORINATED POLYMER CATALYST

[75] Inventor: James D. McClure, Houston, Tex.

[73] Assignee: Shell Oil Company, Houston. Tex.

[21] Appl. No.: 752,350

[22] Filed: Dec. 20, 1976

Related U.S. Application Data

[62] Division of Ser. No. 663,897, March 4, 1976.

[51] Int. Cl.² ................................................ C07C 3/52
[52] U.S. Cl. .............................. 260/671 R; 260/671 C
[58] Field of Search ........................ 260/671 C, 671 R

[56] References Cited

U.S. PATENT DOCUMENTS

| 2,802,884 | 8/1957 | D'Alelio | 260/671 C |
| 3,708,553 | 1/1973 | Olah | 260/671 C |

*Primary Examiner*—C. Davis
*Attorney, Agent, or Firm*—Dean F. Vance

[57] ABSTRACT

A process and catalyst for the preparation of ethylbenzene is disclosed. The catalyst is an unsupported solid perfluorinated polymer containing pendent sulfonic acid groups.

3 Claims, No Drawings

ETHYLBENZENE PROCESS USING AN UNSUPPORTED PERFLUORINATED POLYMER CATALYST

This is a division, of application Ser. No. 663,897, filed Mar. 4, 1976.

BACKGROUND OF THE INVENTION

Hydrocarbon conversion and the isomerization of hydrocarbons in particular, is of special importance to the petroleum industry. In recent years, with the advent of catalytic converters in automobiles and the required use of non-leaded gasoline, a need has arisen for higher octane number gasolines. Natural straight-run gasolines, i.e., naphthas, contain, chiefly, normal paraffins, such as normal pentane and normal hexane, which have relatively low octane numbers. It has become essential, therefore, to convert these low octane components to their higher octane counterparts. The isomerization of these hydrocarbon components accomplish this conversion, i.e., the isomers resulting have a much higher octane rating. Hence, the facility with which this isomerization is accomplished has become of prime importance.

Likewise, the need for isoparaffins, benzene, xylene, and ethyl benzene as building components in the petrochemical industry is increasing. Accordingly, the need for improved hydrocarbon conversion processes in the petrochemical industry is also great.

One of the primary hydrocarbon conversion processes now employed is the alkylation of isoparaffins. It was thought that certain sulfonated fluorocarbon polymers possess sufficient activity and stability to be useful as alkylation catalysts. However, in a recent study by Kapura and Gates, Sulfonated Polymers as Alkylation Catalysts, Industrial Engineering Chemistry Product Research Development, Vol. 12, No. 1, pp. 62–66 (1973), it was found that a sulfonated fluorocarbon vinyl ether polymer was inactive in alkylating isobutane with propylene in the gas phase and in a mole ratio of 5 to 1 at 260° C. The conclusion reached in that study was that the sulfonated fluorocarbon vinyl ether polymer catalyst was too weakly acidic to catalyze paraffin alkylation and that the polymer was not a useful catalyst. That study also showed that these same ion exchange resins were useful in the alkylation of benzene with propylene in the vapor phase to form cumene. However, the conclusion reached by Kapura and Gates with regard to the formation of cumene was that the sulfonated polymer was not "a particularly useful catalyst at temperatures greater than about 150° C." Contrary to the conclusions reached by Kapura and Gates, it has now been found that a perfluorinated polymer containing pendant sulfonic acid groups is a very active catalyst in the preparation of ethylbenzene from benzene and ethylene, in the alkylation of isoparaffins, in the isomerization of normal alkanes, and in the disproportionation of toluene.

SUMMARY OF THE INVENTION

The present invention comprises an improved hydrocarbon conversion process which comprises contacting said hydrocarbons under hydrocarbon converting conditions with an unsupported perfluorinated polymer catalyst containing a repeating structure selected from the group consisting of:

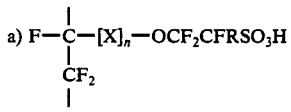

I or

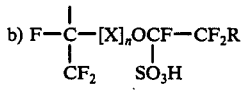

II where n is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical.

DETAILED DESCRIPTION OF THE INVENTION

A. The Catalyst

The catalyst employed in the present invention is a solid at reaction conditions. The catalyst broadly comprises a perfluorinated polymer having acid groups in the amount of about 0.01 to 5 mequiv/gram catalyst. Preferably, the polymer contains about 0.05 to 2 mequiv/gram of catalyst.

In a specific embodiment, the polymer catalyst contains a repeating structure selected from the group consisting of:

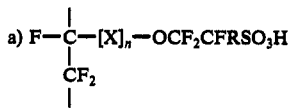

I or

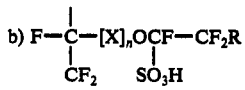

II where n is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical. In a preferred embodiment, n is 1 or 2, Y is a trifluoromethyl radical, R is fluorine, and $m$ is 2. Catalysts of the above-noted structure typically have a molecular weight of between about 1,000 and 500,000 daltons.

Polymer catalysts of the above-noted structure can be prepared in various ways. One method, disclosed in Connolly et al, U.S. Pat. No. 3,282,875 and Cavanaugh et al, U.S. Pat. No. 3,882,093, comprises polymerizing vinyl compounds of the formula:

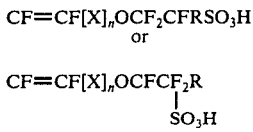

in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from $-50°$ to $+200°$ C depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of structure III or IV in an aqueous medium using a peroxide or a redox initiator. The polymerization methods employed correspond to those established in the art for the polymerization of tetrafluoroethylene in aqueous media.

It is also possible to prepare catalysts for the present invention by copolymerizing the vinyl ethers of structure III or IV with perfluoroethylene and/or perfluoroalpha-olefins. A preferred copolymer prepared by polymerizing perfluoroethylene with a perfluorovinyl ether containing attached sulfonic acid groups would have the following structure:

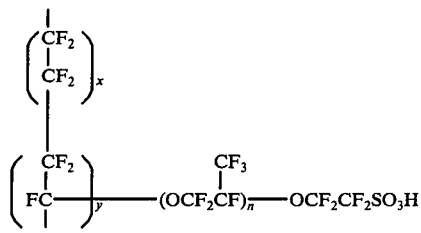

wherein $n = 1$ or 2 and the ratio of x over y varies from about 2 to about 50. The polymer of structure V is available commercially under the tradename of NAFION resin. Catalysts of the above-noted structure V offer the advantages of high concentrations of accessible acid groups in a solid phase.

B. Preparation of Ethylbenzene

As is well known to those skilled in the art, ethylbenzene is a desirable article of commerce since it is the starting material for the production of styrene. Generally, styrene is produced through the steam dehydrogenation of ethylbenzene. Ethylbenzene does occur, to some extent, in petroleum fractions and may be obtained from such fractions through the technique of super-distillation. However, the demand for styrene in recent times has far surpassed the availability of naturally occurring ethylbenzene. Accordingly, the prior art has resorted more and more to the alkylation of benzene with ethylene using various types of catalyst. Among the catalysts employed in the prior art are aluminum chloride, U.S. Pat. No. 3,848,012; phosphoric acid, U.S. Pat. No. 3,478,119; boron trifluoride-modified alumina, British Pat No. 905,051; silica-alumina, U.S. Pat. No. 2,419,796; and zeolites, U.S. Pat. No. 3,751,504.

It is also known that certain sulfonated fluorocarbon vinyl ether polymers are useful in the alkylation of benzene with propylene in the vapor phase to form cumene. See the recent study by Kapura and Gates, supra. However, the conclusion reached by Kapura and Gates in their study was that the sulfonated polymer was not "a practically useful catalyst at temperatures greater than about 150° C. Contrary to the conclusions reached by Kapura and Gates for employing sulfonated polymers to prepare cumene from benzene and propylene, it has now been found that catalysts of the instant invention are very active in the preparation of ethylbenzene from benzene and ethylene. This finding is especially surprising since it is well known that propylene is more reactive than ethylene.

In the present invention, ethylene is reacted with benzene in the liquid phase over the present catalyst and at a temperature of between about 125° and 225° C. The catalysts and process of the present invention produce an ethylbenzene product containing very little (less than 0.1%) cumene, and with a relatively high percentage of ethylbenzene in the reaction zone affluent.

The ethylene feed stream suitable for use in the practice of the present invention may be either of high purity or of a lower purity. High purity ethylene streams comprise at least 90 mol percent ethylene, preferably over about 95 mol percent ethylene. However, it is often useful to employ lower purity ethylene streams. Preferred ethylene streams contain between about 35 and about 75 percent ethylene, usually less than about 50 percent ethylene, with the balance of the stream being largely inert gases such as ethane, methane and hydrogen. However, with either high or low purity ethylene, the ethylene feed stream should be substantially free from aromatics, acetylene, and other olefins.

The benzene to be used in the present invention should be of relatively high purity. However, the benzene is typically obtained from storage facilities and, therefore, will often be saturated with water. Contrary to the detrimental effect of water on the commercially used aluminum chloride and silica-alumina catalysts, water levels of as high as 100 ppm have no detrimental effect on the catalysts of the present invention.

In order to prevent polymerization of the ethylene, an excess of benzene is used. The mole ratio of benzene to ethylene, varies from about 1.5:1 to about 10:1, preferably about 2:1 to about 5:1.

The process may be carried out either as a batch or continuous type of operation, although it is preferred to carry out the process continuously. It has been generally established that the more intimate the contact between the feedstock and the catalyst, the better the yield of desired product obtained. With this in mind, the present process, when operated as a batch operation, is characterized by the use of vigorous mechanical stirring or shaking of the reactants and catalyst.

When employing a continuous process, the feed streams may be contacted with the catalyst in any suitable reactor. In one embodiment, the catalyst is packed in a vertical, tubular reactor bed with inert supports, such as ceramic balls or silicon carbide, above and below the catalyst. the catalyst can be mixed with an inert material, such as quartz, and loaded in the reactor so as to improve the fluid dynamics of the system. The flow of the reactant feed stream may be upflow or downflow, with an upflow arrangement being preferred to ensure liquid phase alkylation.

Reaction temperature is varied between about 125° and about 225° C. The reaction temperature must be kept below about 225° C due to the lack of stability of the catalyst at temperatures of over 250° C. A preferred temperature range is between about 150° C and about 210° C. In general, the activity of the catalyst is greater at the higher temperatures. That is, as temperature increases, the conversion of ethylene increases.

In general, the pressure in the reaction zone is maintained to keep the reactants in the liquid phase, and accordingly, will vary with the particular reactants employed and the reaction temperatures. Typical reaction zone pressure varies from about 10 psig to about 2,000 psig.

The weight hourly space velocity effectively measures the catalyst concentration employed, and hence, also measures the relative activity of the catalyst. Weight hourly space velocity (WHSV) is defined as the weight per hour of total combined feed (benzene plus ethylene) divided by the weight of catalyst employed. Thw WHSV varies between about 0.5 hr$^{-1}$ and about 20 hr$^{-10}$, preferably about 2 hr$^{-1}$ and about 10 hr$^{-1}$.

The invention is further illustrated by means of the following Illustrative Embodiment which is given for the purpose of illustration only, and the invention is not to be regarded as limited to any of the specific materials or conditions recited therein.

In Illustrative Embodiment Ic, the reactor employed was a 17-inch stainless steel tube equipped with a liquid feed upflow inlet. The catalyst bed occupied the central portion of the reactor, with several grams of carborundum chips on both sides of the catalyst bed to prevent entrainment of the catalyst. All reactions took place in the liquid phase.

Illustrative Embodiment Ic

The catalyst employed in Illustrative Embodiment Ic was prepared by grinding Nafion XR granules with a blender to 150 micrometer or less particle size. The ground material was then treated twice with 30% sulfuric acid to convert the material from a potassium (K+) form to the H+ form. The treated material was collected by filtration, washed with distilled water until the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

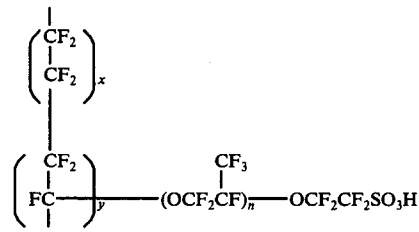

About 4.0 grams of the resulting polymer catalyst was mixed with 5.0 grams of quartz and loaded in the reactor. Reaction conditions were a pressure of 500 psig, a temperature of 175° C and an approximate benzene/ethylene mole ratio of 5:1. The weight hourly space velocity, WHSV (defined as the grams of total feed per hour divided by the grams of catalyst employed), varied from 1.0 hr$^{-1}$ to 8.0 hr$^{-1}$ as indicated in the results presented below in Table 1c.

Table 1c

| Time, hours | 4 | 24 | 44 | 50 | 74 | 78 |
|---|---|---|---|---|---|---|
| Temperature, ° C | 175 | 175 | 175 | 175 | 176 | 175 |
| WHSV | 1.0 | 1.0 | 1.0 | 2.0 | 4.0 | 8.0 |
| Ethylene Conversion, % | 100 | 100 | 100 | 100 | 100 | 100 |
| Ethylbenzene, %w in product | 15.6 | 15.4 | 15.5 | 16.3 | 16.9 | 17.5 |
| Selectivity, %w | | | | | | |
| Ethylbenzene | 80 | 80 | 80 | 84 | 86 | 88 |
| Butylbenzene | 1 | 1 | 1 | 1 | 1 | 1 |
| Diethylbenzene | 15 | 15 | 14.5 | 12.5 | 11 | 10 |
| Triethylbenzene | 3.6 | 3.1 | 3.5 | 2.1 | 1.8 | 1.5 |
| Tetraethylbenzene | 1.0 | 1.0 | 1.0 | 0.5 | 0.3 | — |

What is claimed is:

1. A liquid phase process for the preparation of ethylbenzene which comprises contacting an ethylene feed stream with a benzene feed stream at a reaction temperature of between about 125° and about 225° C in the presence of an unsupported solid perfluorinated polymer catalyst wherein said catalyst contains a repeating structure selected from the group of:

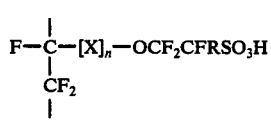

a)

or

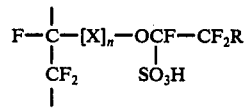

b)

where $n$ is 0, 1 or 2; R is a radical selected from the group consisting of fluorine and perfluoroalkyl radicals having from 1 to 10 carbon atoms; and X is selected from the group consisting of:

[O(CF$_2$)$_m$], [OCF$_2$CFY] or [OCFYCF$_2$]

where $m$ is an integer from 2 to 10 and Y is a radical selected from the class consisting of fluorine and trifluoromethyl radical.

2. A process according to claim 1 wherein the mole ratio of said benzene stream to said ethylene stream varies from about 1.5:1 to about 10:1.

3. A process according to claim 1 wherein the weight hourly space velocity, defined as the weight per hour of the reactants divided by the weight of catalyst employed, varies from between about 0.5 to about 20.0 hr$^{-1}$.

* * * * *

Notice of Adverse Decision in Interference

In Interference No. 100,323, involving Patent No. 4,041,090, J. D. McClure, ETHYLBENZENE PROCESS USING AN UNSUPPORTED PERFLUORINATED POLYMER CATALYST, final judgment adverse to the patentee was rendered Sept. 11, 1980 as to claims 1–3.

[*Official Gazette November 18, 1980.*]